(12) United States Patent
Hill

(10) Patent No.: US 6,752,151 B2
(45) Date of Patent: Jun. 22, 2004

(54) METHOD AND APPARATUS FOR PROVIDING VARIABLE POSITIVE AIRWAY PRESSURE

(75) Inventor: Peter D. Hill, Monroeville, PA (US)

(73) Assignee: Respironics, Inc., Murrysville, PA (US)

( * ) Notice: Subject to any disclaimer, the term of this patent is extended or adjusted under 35 U.S.C. 154(b) by 61 days.

(21) Appl. No.: 09/957,057

(22) Filed: Sep. 20, 2001

(65) Prior Publication Data

US 2002/0088465 A1 Jul. 11, 2002

Related U.S. Application Data

(60) Provisional application No. 60/235,015, filed on Sep. 25, 2000.

(51) Int. Cl.$^7$ .............................. A61M 16/00; A62B 7/00
(52) U.S. Cl. .............................. 128/204.18; 128/204.21; 128/204.23
(58) Field of Search ........................ 128/204.18, 204.21, 128/204.23, 205.23

(56) References Cited

U.S. PATENT DOCUMENTS

| | | | |
|---|---|---|---|
| 5,398,682 A | 3/1995 | Lynn | |
| 5,535,738 A | * 7/1996 | Estes et al. | 128/204.23 |
| 5,647,345 A | 7/1997 | Saul | |
| 5,794,615 A | 8/1998 | Estes | |
| 5,803,065 A | * 9/1998 | Zdrojkowski et al. | 128/204.23 |
| 6,105,575 A | 8/2000 | Estes et al. | |
| 6,119,686 A | * 9/2000 | Somerson et al. | 128/202.22 |
| 6,575,163 B1 | * 6/2003 | Berthon-Jones | 128/204.18 |

FOREIGN PATENT DOCUMENTS

WO  WO 99/61088  12/1999

* cited by examiner

Primary Examiner—Glenn K. Dawson
Assistant Examiner—Darwin P. Erezo
(74) Attorney, Agent, or Firm—Michael W. Haas

(57) ABSTRACT

A method and apparatus for treating a breathing disorder and, more particularly, a method and apparatus for providing a pressurized air flow to an airway of a patient to treat congestive heart failure in combination with Cheyne-Stokes respiration and/or sleep apnea or other breathing disorders. A positive airway pressure ventilator is utilized in combination with an algorithm that adjusts IPAP and EPAP in order to counter a Cheyne-Stokes breathing pattern. Cheyne-Stokes respiration is detected by monitoring a peak flow of the patient.

14 Claims, 10 Drawing Sheets

DELTA TARGET PEAK FLOW DECISION TABLE 113

| # | CSR SHAPE INDEX, % | | | CSR SEVERITY INDEX, % | | | | PS INDEX, % | | | | DELTA TARGET PEAK FLOW |
|---|---|---|---|---|---|---|---|---|---|---|---|---|
| | 0-50 | 51-60 | 61-100 | 0-25 | 26-50 | 51-75 | 76-100 | 0-25 | 26-50 | 51-75 | 76-100 | LPM |
| 0 | X | | | X | | | | X | | | | 0 |
| 1 | X | | | X | | | | | X | | | -1 |
| 2 | X | | | X | | | | | | X | | -2 |
| 3 | X | | | X | | | | | | | X | -2 |
| 4 | X | | | | X | | | X | | | | 0 |
| 5 | X | | | | X | | | | X | | | -1 |
| 6 | X | | | | X | | | | | X | | -1 |
| 7 | X | | | | X | | | | | | X | -2 |
| 8 | X | | | | | X | | X | | | | 0 |
| 9 | X | | | | | X | | | X | | | -1 |
| 10 | X | | | | | X | | | | X | | -2 |
| 11 | X | | | | | X | | | | | X | -2 |
| 12 | X | | | | | | X | X | | | | 0 |
| 13 | X | | | | | | X | | X | | | -2 |
| 14 | X | | | | | | X | | | X | | -2 |
| 15 | X | | | | | | X | | | | X | -3 |
| 16 | | X | | X | | | | X | | | | 2 |
| 17 | | X | | X | | | | | X | | | 1 |
| 18 | | X | | X | | | | | | X | | 0 |
| 19 | | X | | X | | | | | | | X | -1 |
| 20 | | X | | | X | | | X | | | | 1 |
| 21 | | X | | | X | | | | X | | | 0 |
| 22 | | X | | | X | | | | | X | | 0 |
| 23 | | X | | | X | | | | | | X | -1 |
| 24 | | X | | | | X | | X | | | | 0 |
| 25 | | X | | | | X | | | X | | | 0 |
| 26 | | X | | | | X | | | | X | | -1 |
| 27 | | X | | | | X | | | | | X | -1 |
| 28 | | X | | | | | X | X | | | | 0 |
| 29 | | X | | | | | X | | X | | | -1 |
| 30 | | X | | | | | X | | | X | | -2 |
| 31 | | X | | | | | X | | | | X | -2 |
| 32 | | | X | X | | | | X | | | | 3 |
| 33 | | | X | X | | | | | X | | | 2 |
| 34 | | | X | X | | | | | | X | | 1 |
| 35 | | | X | X | | | | | | | X | 1 |
| 36 | | | X | | X | | | X | | | | 2 |
| 37 | | | X | | X | | | | X | | | 2 |
| 38 | | | X | | X | | | | | X | | 1 |
| 39 | | | X | | X | | | | | | X | 1 |
| 40 | | | X | | | X | | X | | | | 1 |
| 41 | | | X | | | X | | | X | | | 0 |
| 42 | | | X | | | X | | | | X | | 0 |
| 43 | | | X | | | X | | | | | X | -1 |
| 44 | | | X | | | | X | X | | | | 0 |
| 45 | | | X | | | | X | | X | | | 0 |
| 46 | | | X | | | | X | | | X | | -1 |
| 47 | | | X | | | | X | | | | X | -1 |

FIG. 7

DELTA EPAP DECISION TABLE                    115

| | CSR SHAPE INDEX, % | | | CSR SEVERITY INDEX, % | | | | PS INDEX, % | | | | DELTA EPAP |
|---|---|---|---|---|---|---|---|---|---|---|---|---|
| | 0-50 | 51-60 | 61-100 | 0-25 | 26-50 | 51-75 | 76-100 | 0-25 | 26-50 | 51-75 | 76-100 | CMH2O |
| 0 | X | | | X | | | | X | | | | 1 |
| 1 | X | | | X | | | | | X | | | 1 |
| 2 | X | | | X | | | | | | X | | 1 |
| 3 | X | | | X | | | | | | | X | 1 |
| 4 | X | | | | X | | | X | | | | 1 |
| 5 | X | | | | X | | | | X | | | 1 |
| 6 | X | | | | X | | | | | X | | 1 |
| 7 | X | | | | X | | | | | | X | 1 |
| 8 | X | | | | | X | | X | | | | 0 |
| 9 | X | | | | | X | | | X | | | 0 |
| 10 | X | | | | | X | | | | X | | 0 |
| 11 | X | | | | | X | | | | | X | 0 |
| 12 | X | | | | | | X | X | | | | 0 |
| 13 | X | | | | | | X | | X | | | 0 |
| 14 | X | | | | | | X | | | X | | 0 |
| 15 | X | | | | | | X | | | | X | 0 |
| 16 | | X | | X | | | | X | | | | 1 |
| 17 | | X | | X | | | | | X | | | 1 |
| 18 | | X | | X | | | | | | X | | 1 |
| 19 | | X | | X | | | | | | | X | 1 |
| 20 | | X | | | X | | | X | | | | 1 |
| 21 | | X | | | X | | | | X | | | 1 |
| 22 | | X | | | X | | | | | X | | 1 |
| 23 | | X | | | X | | | | | | X | 1 |
| 24 | | X | | | | X | | X | | | | 1 |
| 25 | | X | | | | X | | | X | | | 1 |
| 26 | | X | | | | X | | | | X | | 1 |
| 27 | | X | | | | X | | | | | X | 1 |
| 28 | | X | | | | | X | X | | | | 0 |
| 29 | | X | | | | | X | | X | | | 0 |
| 39 | | X | | | | | X | | | X | | 0 |
| 31 | | X | | | | | X | | | | X | 0 |
| 32 | | | X | X | | | | X | | | | 2 |
| 33 | | | X | X | | | | | X | | | 2 |
| 34 | | | X | X | | | | | | X | | 2 |
| 35 | | | X | X | | | | | | | X | 2 |
| 36 | | | X | | X | | | X | | | | 1 |
| 37 | | | X | | X | | | | X | | | 1 |
| 38 | | | X | | X | | | | | X | | 1 |
| 39 | | | X | | X | | | | | | X | 1 |
| 40 | | | X | | | X | | X | | | | 1 |
| 41 | | | X | | | X | | | X | | | 1 |
| 42 | | | X | | | X | | | | X | | 1 |
| 43 | | | X | | | X | | | | | X | 1 |
| 44 | | | X | | | | X | X | | | | 1 |
| 45 | | | X | | | | X | | X | | | 1 |
| 46 | | | X | | | | X | | | X | | 1 |
| 47 | | | X | | | | X | | | | X | 1 |

FIG. 8

METHOD AND APPARATUS FOR PROVIDING VARIABLE POSITIVE AIRWAY PRESSURE

CROSS-REFERENCE TO RELATED APPLICATIONS

This application claims priority under 35 U.S.C. §119(e) from provisional U.S. patent application Ser. No. 60/235,015 filed Sep. 25, 2000, the contents of which are incorporated herein by reference.

BACKGROUND OF THE INVENTION

1. Field of the Invention

The present invention relates generally to a method and apparatus for providing a positive pressure therapy particularly suited treat a patient suffering from congestive heart failure, and, more particularly, to a method and apparatus for providing a pressurized flow of breathing gas to an airway of a patient to treat Cheyne-Stokes respiration, sleep apnea, or other breathing disorders commonly associated with congestive heart failure.

2. Description of the Related Art

Congestive heart failure (CHF) patients commonly suffer from respiratory disorders, such as obstructive sleep apnea (OSA). Another such respiratory disorder CHF patients often experience during sleep is known as Cheyne-Stokes respiration. FIG. 1 illustrates a typical Cheyne-Stokes respiration (CSR) pattern 30, which is characterized by rhythmic waxing periods 32 and waning periods 34 of respiration, with regularly recurring periods of high respiratory drive (hyperpnea) 36 and low respiratory drive (hypopnea or apnea) 38. A typical Cheyne-Stokes cycle, generally indicated at 40 in FIG. 1, lasts about one minute and is characterized by a crescendo (arrow A), in which the peak respiratory flow of the patient increases over several breath cycles, and decrescendo (arrow B) variation in peak flow, in which the peak respiratory flow of the patient decreases over several breath cycles. The disruption in sleep, as well as the periodic desaturation of arterial oxygen ($PaO_2$), stresses the cardio-vascular system and specifically the heart. Hyperpnea often causes arousals and, thus, degrades sleep quality.

Relatively recent developments in the treatment of sleep apnea includes the use of continuous positive airway pressure (CPAP), which is the application of a constant pressure to the airway of a patient. This type of positive airway pressure therapy has been applied not only to the treatment of breathing disorders, but also to the treatment of CHF. In using CPAP on a CHF patient, the effect of the CPAP is to raise the pressure in the chest cavity surrounding the heart, which allows cardiac output to increase.

Bi-level positive airway pressure therapy is a form of positive airway pressure therapy that has been advanced in the treatment of sleep apnea and other breathing and cardiac disorders. In a bi-level pressure support therapy, pressure is applied to the airway of a patient alternately at relatively higher and lower pressure levels so that the therapeutic pressure is alternately administered at a larger and smaller magnitude force. The higher and lower magnitude positive prescription pressure levels are known as IPAP (inspiratory positive airway pressure) and EPAP (expiratory positive airway pressure), and are synchronized with the patient's inspiratory cycle and expiratory cycle, respectively.

A publication entitled "Effects of Continuous Positive Airway Pressure on Cardiovascular Outcomes in Heart Failure Patients With and Without Cheyne-Stokes Respiration," by Don D. Sin et al., which was published on Jul. 4, 2000 in Circulation, Vol. 102, pp. 61–66, describes how CPAP improves cardiac output in patients suffering from CHF and having both CSR and central sleep apnea (CSA), which is a cessation of breathing for a period of time not due to an obstruction of the airway. Additionally, it was found that CPAP can reduce the combined mortality-cardiac transplantation rate in patients with combined CSR-CSA who comply with CPAP therapy.

One approach to providing a pressure support therapy for the treatment of cardiac failure, CSR, or CSA is described in International Patent Application Publication No. WO 99/61088 to Resmed Limited ("the '088 publication"). According to the teachings of the '088 publication, a patient is provided with a ventilatory or pressure support using a blower and mask in much the same way as a conventional bi-level pressure support system. However, the system also derives an instantaneous ventilation of the patient by measuring the volume inspired, the volume expired, or half an average volume of the respiratory airflow over a short period of time. This derived measure of instantaneous ventilation is then used to adjust the level of ventilatory support in an attempt to reduce or eliminate short term changes in the derived measure of instantaneous ventilation. This is accomplished by comparing the derived measure of instantaneous ventilation with a target ventilation, which is a relatively long term measure, and controlling the level of pressure support based on the error between the two.

There are disadvantages associated with this method of providing pressure support to a patient to treat cardiac failure, CSR, or CSA. For example, in many situations, the average value of the past tidal volumes of the patient will not produce a target ventilation that, in turn, will result in sufficient treatment of the hypopneas and hyperpneas to counteract the occurrence of CSR. This is believed to be true because CSR has a continuum of severity and, depending on the level of severity, the target ventilation needs to be adjusted to values other than the average of the last 1–2 minutes. Moreover, the CHF patient may have some degree of obstruction that must be treated for its own sake, but also because these obstructive events appear to drive the CSR pattern as well. Therefore, a system that sets a target ventilation based on a long-term average of the past volumes does not address the interplay of obstructing airways and CSR. Using the instantaneous volume as the feedback variable requires yet another calculation, and this calculation is prone to errors due to small errors in the estimated patient flow and detecting the onset and termination of inspiration.

It is, therefore, desirable to provide a method and apparatus for treating OSA and CSR commonly found in the CHF population that adjusts the inspiratory and expiratory pressures to resolve the CSR and OSA based on detecting the peak flow where the effect of the error in the estimated patient flow is always smaller than that in the subsequent volume calculation. It is further desirable to detect the presence and severity of CSR and the level of pressure support presently intervening to treat the CSR more effectively than possible using conventional techniques.

SUMMARY OF THE INVENTION

Accordingly, the present invention provides a method and apparatus for treating sleep apnea and CSR often found in CHF patients that does not suffer from the disadvantages associated with present pressure support treatment techniques. Specifically, the present invention implements many of the standard functions of a positive airway pressure support device, as well as an algorithm that adjusts IPAP, EPAP, or both in order to counter a CSR pattern. The pressure support system includes a pressure generating system and a patient circuit coupled to the pressure generating system. The pressure generating system includes a pressure generating and a pressure controller, such as a valve, to control the flow of breathing gas from the pressure generator. The pressure support system includes a flow sensor to measure the flow of breathing gas in the patient circuit, and a controller to implement the algorithm. The output of the flow sensor is used to determine the peak flow during the patient's respiratory cycles. The detected peak flows are monitored to determine whether the patient is experiencing Cheyne-Stokes breathing.

Determining and delivering the appropriate IPAP and EPAP is a three layer process each with its own time frame. The first process is executed typically 100 times a second and utilizes the aforementioned pressure support system that synchronizes delivery of IPAP and EPAP with the patient's inspiratory and expiratory drive, respectively. In addition to the ventilatory functions, the first process also monitors peak flow and time capture. The second process is executed every breath cycle, which is typically 10–30 times a minute, and determines the IPAP setting for the next inspiratory effort based on the previous peak flow and a target peak flow. The third process is executed every 2 to 5 minutes and computes indices of CSR shape and severity and the persistence of the level of pressure support. The CSR shape index is a measure of how much the last 2–3 minutes of peak flows resembles a typical CSR pattern. The CSR severity index is a ratio of the minimum peak flow over the maximum peak flow during the last 2 to 3 minutes. The pressure support persistence is the percentage of breaths that received a clinically significant level of pressure support, typically 2 cmH$_2$O or greater, over 2 CSR cycles. Based on the CSR shape and severity indices and the pressure support persistence, the third process will adjust either the target peak flow, the EPAP or both.

The level of pressure support is adjusted based on the difference between a target peak flow and the last peak flow times a gain. Increases and decreases to the pressure support are limited to typically 3 cmH$_2$O in order to prevent arousals.

The values for the target peak flow and the timed back up rate can be selected either by manual control or automatically by compiling statistics on the flow waveform and measuring the level and persistence of pressure support that the unit is delivering.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIG. 7 is an exemplary embodiment of a look-up table used to adjust the target peak flow in the process shown in FIG. 3;

FIG. 8 is an exemplary embodiment of a look-up table used to adjust the EPAP level in the process shown in FIG. 3.

DETAILED DESCRIPTION OF THE PRESENTLY PREFERRED EMBODIMENTS OF THE INVENTION

Figure 2:
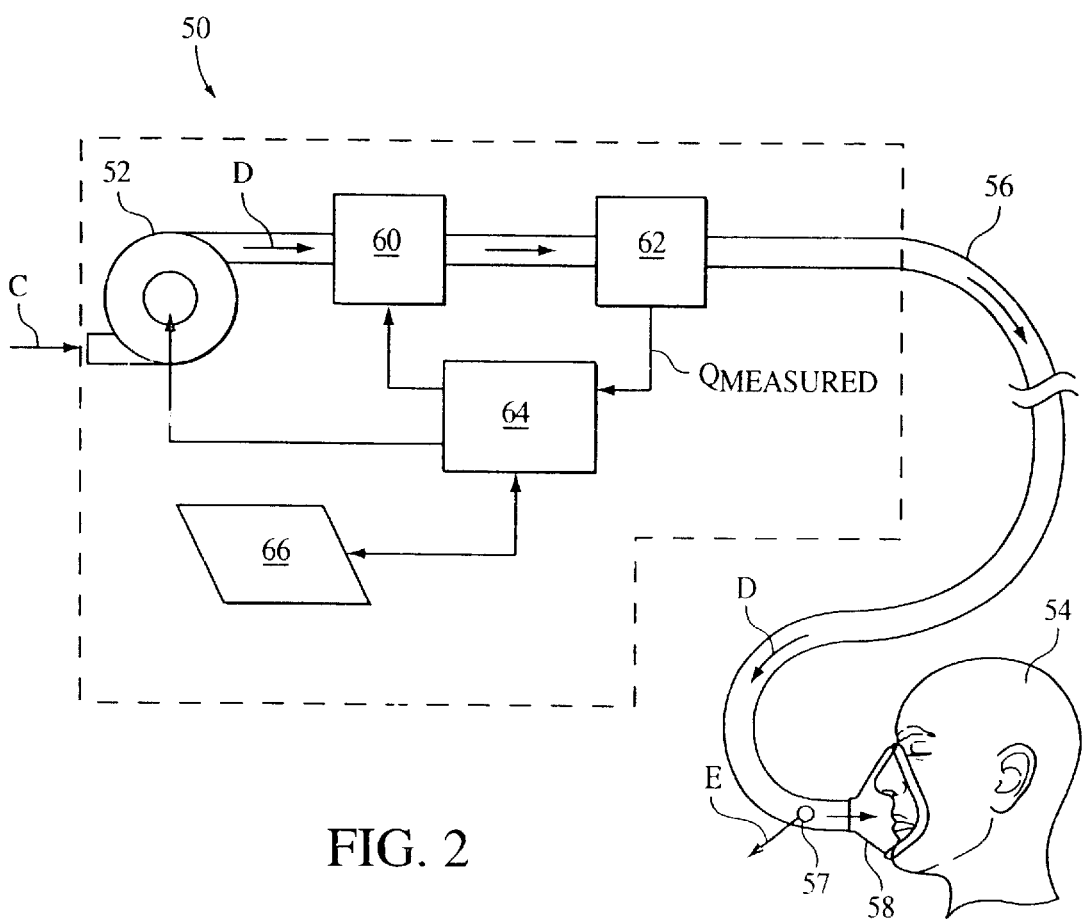
FIG. 2 is a functional block diagram of a variable positive airway pressure support system according to the principles of the present invention.

There is generally indicated at 50 in FIG. 2 a variable positive airway pressure support system according to a presently preferred embodiment of the instant invention and shown in the form of a functional block diagram. Pressure support system 50 is operable to implement a novel mode of pressure support, referred to herein as a variable positive airway pressure (VarPAP) mode, for delivering a flow of breathing gas for the treatment of Cheyne-Stokes respiration.

Variable positive airway pressure support system 50 includes a gas flow generator 52, such as a blower used in a conventional CPAP or bi-level pressure support device, that receives breathing gas, generally indicated by arrow C, from any suitable source, e.g., a pressurized tank of oxygen or air, the ambient atmosphere, or a combination thereof. Gas flow generator 52 generates a flow of breathing gas, such as air, oxygen, or a mixture thereof, for delivery to an airway of a patient 54 at relatively higher and lower pressures, i.e., generally equal to or above ambient atmospheric pressure. The pressurized flow of breathing gas, generally indicated by arrow D from gas flow generator 52 is delivered, via a delivery conduit 56, to a breathing mask or patient interface 58 of any known construction, which is typically worn by or otherwise attached to a patient 54 to communicate the flow of breathing gas to the airway of the patient. Delivery conduit 56 and patient interface device 58 are typically collectively referred to as a patient circuit.

Variable positive airway pressure support system is illustrated in FIG. 2 as a single-limb system, meaning that the patient circuit includes only a delivery conduit 56 connecting the patient to the pressure support device. As such, an exhaust vent 57 is provided in the delivery conduit for venting exhaled gasses from the system as indicated by arrow E. It should be noted that the exhaust vent can be provided at other locations in addition to or instead of in the delivery conduit, such as in the patient interface device. It should also be understood that the exhaust vent can have a wide variety of configurations depending on the desired manner in which gas is to be vented from the pressure support system.

The present invention also contemplates that the variable positive airway pressure support system can be a two-limb system, having a delivery conduit and an exhaust conduit connected to the patient. In a two-limb system, the exhaust conduit carries exhaust gas from the patient and include an exhaust valve at the end distal from the patient. The exhaust valve is typically actively controlled to maintain a desired level or pressure in the system, which is commonly known as positive end expiratory pressure (PEEP).

In the illustrated exemplary embodiment of the present invention, patient interface 58 is a nasal mask. It is to be understood, however, that patient interface 58 can include a nasal/oral mask, nasal pillows, tracheal tube, endotracheal tube, or any other device that provides the gas flow communicating function. Also, for purposes of the present invention, the phrase "patient interface" can include delivery conduit 56 and any other structures that connects the source of pressurized breathing gas to the patient.

In the illustrated embodiment, variable positive airway pressure support system 50 includes a pressure controller in the form of a valve 60 provided in delivery conduit 56. Valve 60 controls the pressure of the flow of breathing gas from flow generator 52 delivered to the patient. For present purposes, flow generator 52 and valve 60 are collectively referred to a pressure generating system because they act in concert to control the pressure and/or flow of gas delivered to the patient.

It should be apparent that other techniques for controlling the pressure delivered to the patient by the pressure generator, such as varying the blower speed, either alone or in combination with a pressure control valve, are contemplated by the present invention. Thus, valve 60 is optional depending on the technique used to control the pressure of the flow of breathing gas delivered to the patient. If valve 60 is eliminated, the pressure generating system corresponds to pressure generator 52 alone, and the pressure of gas in the patient circuit is controlled, for example, by controlling the motor speed of the pressure generator.

Variable positive airway pressure support system 50 further includes a flow sensor 62 that measures the flow of breathing gas within delivery conduit 56. In accordance with a presently preferred embodiment shown in FIG. 2, flow sensor 62 is interposed in line with delivery conduit 56, most preferably downstream of valve 60. Flow sensor 62 generates a flow signal $Q_{measured}$ that is provided to a controller 64 and is used by the controller, as discussed below, to determine the flow of gas at the patient $Q_{patient}$. Of course, other techniques for measuring the respiratory flow of the patient are contemplated by the present invention, such as measuring the flow directly at the patient or at other locations along delivery conduit 54, measuring patient flow based on the operation of the pressure generator, and measuring patient flow using a flow sensor upstream of the pressure generator.

An input/output device 66 is provided for setting various parameters used by the variable positive airway pressure support system, as well as for displaying and outputting information and data to a user, such as a clinician or caregiver. It is to be understood that the present invention contemplates providing input/output terminals so that the operation information and data collected by the variable positive airway pressure support system can be monitored and controlled remotely. Controller 64 is preferably a microprocessor that is capable of implementing and executing routines for monitoring characteristics of patient respiration and controlling the flow of breathing gas based thereon as discussed in detail below.

Figure 3:
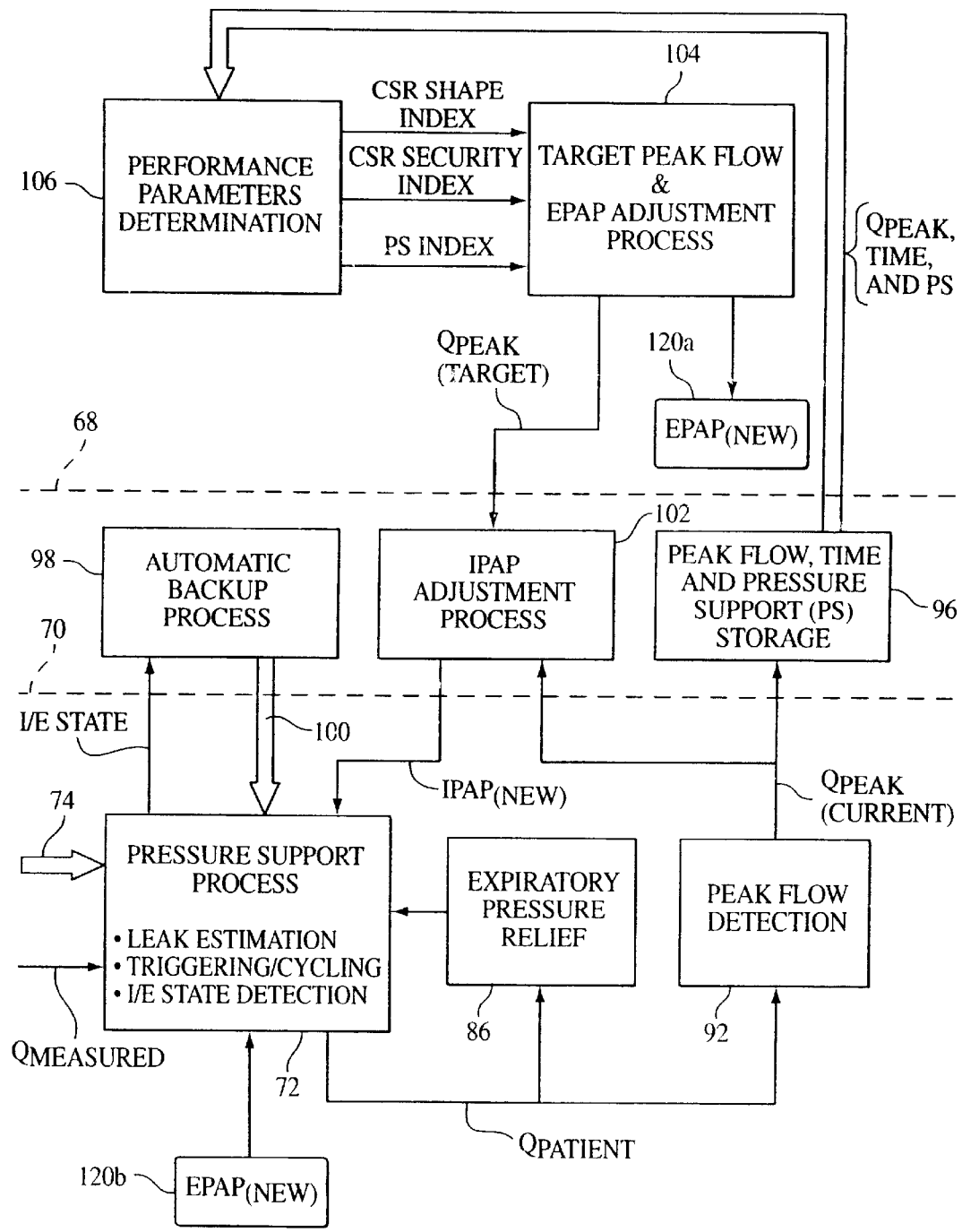
FIG. 3 is a schematic diagram of the process implemented by the pressure support system of FIG. 2 to treat Cheyne-Stokes respiration.

The details of variable positive airway pressure support system 50 and its operation are discussed below with reference to FIGS. 3–10. FIG. 3 schematically illustrates the process carried out by controller 64 in implementing the VarPAP mode of pressure support. Controller 64, in general, performs three sets of processes to manage or control the pressure support delivered to the patient when operating in the VarPAP mode. These three sets of operations are differentiated from one another by lines 68 and 70 in FIG. 3.

The first set of processes, which are below line 70, are carried out essentially continuously by the controller in accordance with the clock speed of the processing unit in controller 64, such as at a rate of 100 Hz. The second set of processes, which are between lines 68 and 70, are carried out less frequently, such as during every respiratory cycle or every other respiratory cycle, typically 10–30 times per minute. They can be executed, for example, at each trigger point, where the pressure support system transitions from EPAP to IPAP, i.e., at the transition from expiration to inspiration, or at each cycle point, where the pressure support system transitions from IPAP to EPAP, i.e., at the transition from inspiration to expiration. The third set of processes, which are above line 68, are carried out even less frequently, such as every 1–5 minutes. In a preferred embodiment of the present invention, the operation above line 68 are carried out every 2 minutes. While the first, second and third sets of operations are described above in the preferred embodiment of the present invention as being executed at a rate of 100 Hz, every breath, and every 2 minutes, respectively. It is to be understood, however, that other rates can be used, so long as the function or functions of each set of operations is sufficiently achieved.

The basic operations of the pressure support system in providing a pressure support therapy to a patient are accomplished by pressure support process block 72 in FIG. 3. In a preferred embodiment of the present invention, the variable positive airway pressure support system essentially functions as a bi-level pressure support system, and, therefore, includes all of the capabilities necessary in such systems in order to provide separate IPAP and EPAP levels to the patient. This includes receiving the necessary parameters via input commands, signals, instructions or information 74 for providing a bi-level pressure, such as maximum and minimum IPAP and EPAP settings. The flow signal $Q_{measured}$ from flow sensor 62 is also provided to the pressure support process, which controls the pressure controller to output the desired inspiratory and expiratory waveforms. Typically, carrying out the pressure support operation includes estimating or determining the actual patient flow $Q_{patient}$ based on the flow signal $Q_{measured}$, determining whether the patient is in the inspiratory or expiratory phase of the respiratory cycle and providing an I/E state signal indicative of the respiratory state of the patient, and triggering and cycling the pressure support system. The outputs to the pressure controller are not illustrated in FIG. 3 for ease of illustration.

In a preferred embodiment of the present invention, which is a single-limb system, controller 64 in process block 72 estimates the leakage of gas from the pressure support system using any conventional technique and incorporates this leak estimation into the determination of the actual patient flow $Q_{patient}$. This leak estimation is required in a single-limb system, because a single-limb system includes a known leak through the exhaust vent as well as other unknown leaks, such as leaks at the patient contact site of the patient interface and at various conduit couplings on the patient circuit. In a two-limb system, leak estimation may not be required, because a flow sensor is typically provided at the exhaust vent to measure, directly, the flow of exhaust gas. In such a system, the patient flow $Q_{patient}$ can be determined by subtracting the measured exhaust flow from the measured flow delivered to the patient. It can be appreciated that leak detection can be performed in a two-limb system to increase the accuracy of the patient flow determination.

U.S. Pat. No. 5,148,802 to Sanders et al., U.S. Pat. No. 5,313,937 to Zdrojkowski et al., U.S. Pat. No. 5,433,193 to Sanders et al., U.S. Pat. No. 5,632,269, to Zdrojkowski et al., U.S. Pat. No. 5,803,065 to Zdrojkowski et al., and U.S. Pat. No. 6,029,664 to Zdrojkowski et al., as well as pending U.S. patent application Ser. No. 09/586,054 to Frank et al., the contents of each of which are incorporated by reference into the present invention, describe how to accomplish the necessary functions in order to provide separate IPAP and EPAP levels to the patient, which are the functions accomplished in process block 27. These functions include techniques for detecting and estimating leak, and techniques for detecting the respiratory state of a patient, and managing, e.g., triggering and cycling, the bi-level delivery of breathing gas to the patient in the presence of leaks. Thus, a detailed discussion of these functions is omitted from the present application for the sake of simplicity and brevity.

Figure 4A:
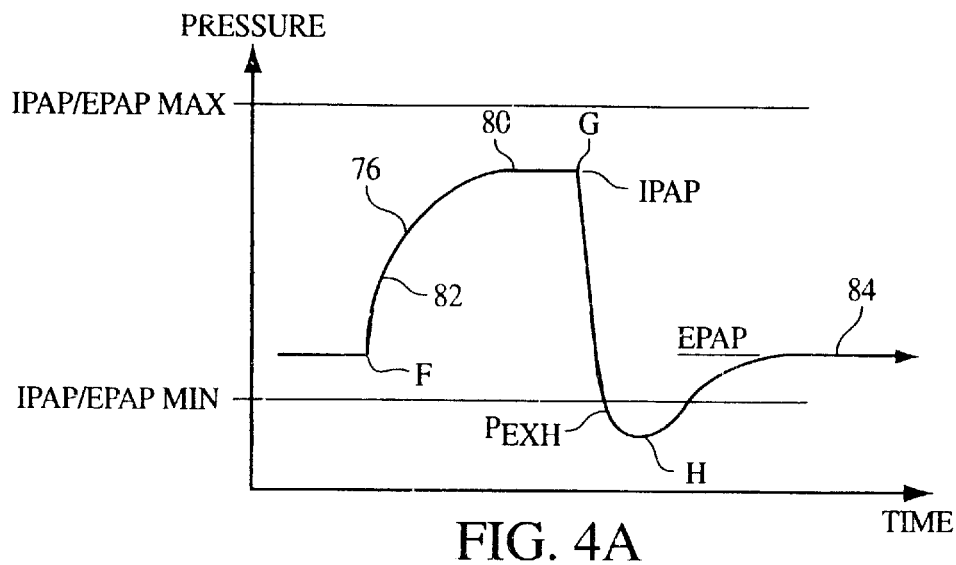
FIGS. 4A, 4B and 4C illustrate pressure waveforms delivered by the pressure support system of FIG. 2 according to the principles of the present invention.

In a preferred embodiment of the present invention, controller 64, in process block 72, controls pressure generator 52, pressure controller 60, or both to deliver a VarPAP waveform 76, as generally shown in FIG. 4A, to an airway of patient 54. VarPAP waveform 76 is essentially a bi-level pressure waveform that alternates between an IPAP level and an EPAP level. According to the present invention, the IPAP and EPAP levels are variable under the controller of controller 64 as discussed below. Therefore, maximum and minimum IPAP and EPAP levels ($IPAP_{max}$, $IPAP_{min}$, $EPAP_{max}$, $EPAP_{min}$) are provided to the controller as inputs 74 to process block 72. It should be understood that the maximum and minimum IPAP and EPAP levels can also be preestablished and stored in the controller as a default or in lieu of input parameters from the system operator. In a preferred embodiment of the present invention, the minimum IPAP level is set to a level that is sufficient to treat OSA.

As shown in FIG. 4A, at time F, which is the trigger point from expiration to inspiration, the patient begins inspiring and triggers the pressure support system to transition to an IPAP level 80. The shape and duration of the pressure increase or rise 82 from trigger point F to the IPAP level can be fixed or variable, as taught for example, in U.S. Pat. Nos. 5,598,838 and 5,927,274 both to Servidio et al. and copending U.S. patent application Ser. No. 60/216,999, to Yurko, the contents of each of which are incorporated herein by reference. It should be understood that the present invention contemplates that the inspiratory portion of pressure waveform 76 can have a variety of configurations.

At time G, at the end of the inspiratory period, which is the cycle point from inspiration to expiration, the patient begins the expiratory phase of the breathing cycle and the pressure support system cycles, causing the pressure to drop toward an EPAP level, indicated at 84. In the illustrated embodiment, the waveform for expiratory pressure, $P_{exh}$, output by the pressure support system during the expiratory phase of the breathing cycle is determined according to the following equation:

$$P_{exh} = EPAP + Gain_{exh} * Flow, \quad (1)$$

where $Gain_{exh}$ is a gain factor, typically selected by a caregiver, and Flow is the estimated patient flow $Q_{patient}$. U.S. Pat. Nos. 5,535,738; 5,794,615; and 6,105,575 all to Estes et al., the contents of which are incorporated herein by reference, teach this technique for controlling the expiratory pressure delivered by a bi-level pressure support system. As a result, the pressure delivered to the patient drops below EPAP at area H during patient exhalation, thereby increasing patient comfort. In FIG. 3, an expiratory pressure relief process 86 receives the patient flow $Q_{patient}$ and implements equation (1) for generating the expiratory pressure waveform $P_{exh}$, which is then supplied to process block 72.

Figure 4B:
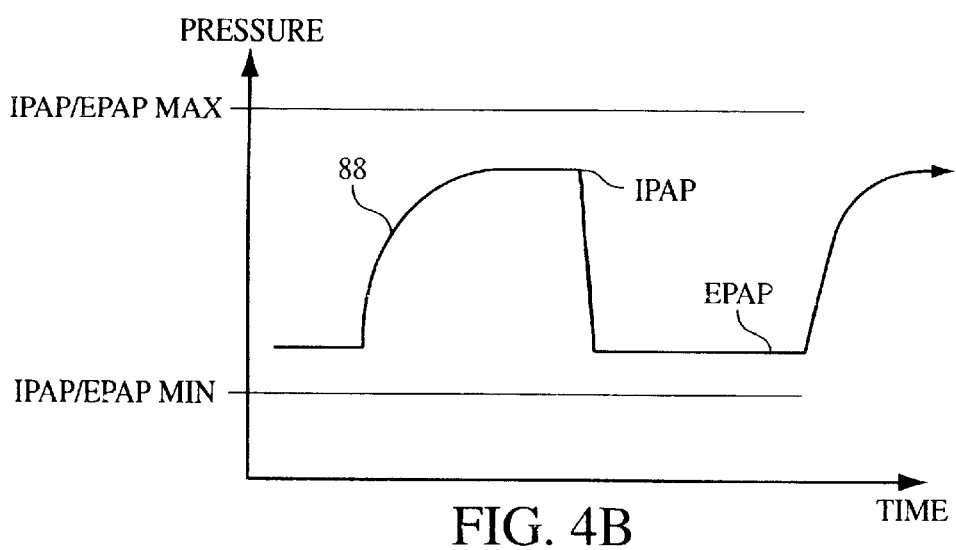
Figure 4C:
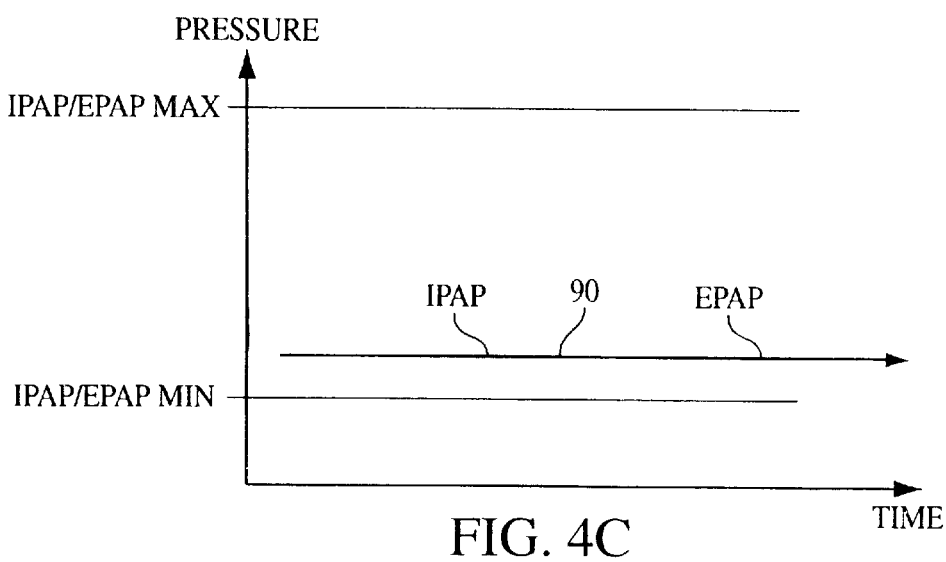
Figure 5A:
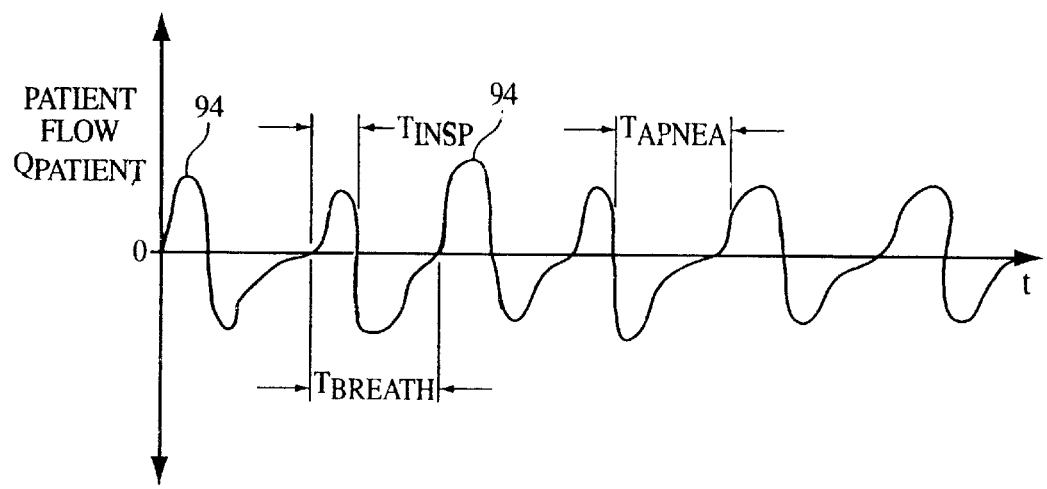
FIG. 5A is a chart illustrating the patient flow for a normal patient and FIG. 5B is a chart illustrating the patient flow for a patient experiencing CSR.
Figure 5B:
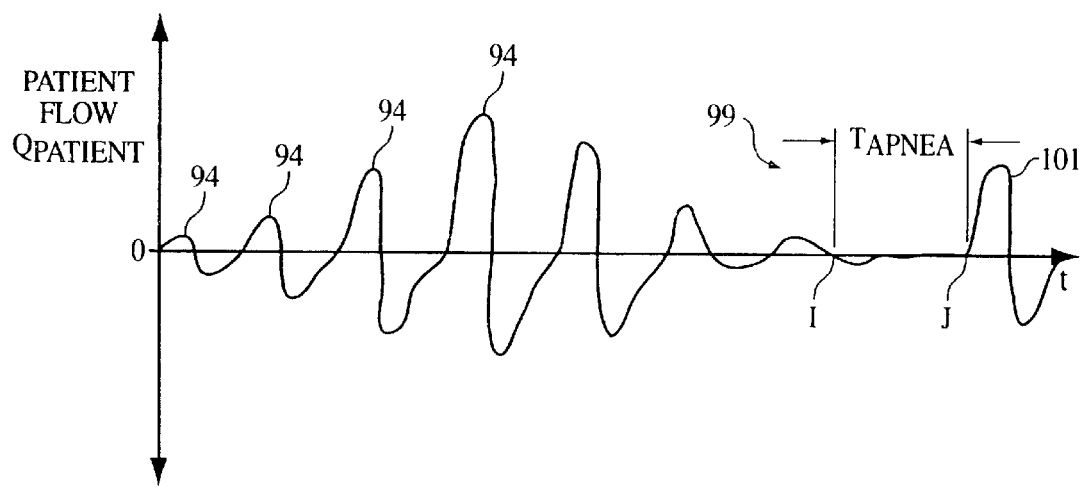

It is to be understood that the present invention contemplates that the expiratory portion $P_{exh}$ of pressure waveform 76 can have a variety of configurations. For example, FIG. 4B illustrates a VarPAP waveform 88 in which the expiratory pressure waveform $P_{exh}$ corresponds to the expiratory pressure administered by a conventional bi-level pressure support system, wherein the EPAP level remain generally constant throughout the expiratory phase of the breathing cycle. This is accomplished, for example, by eliminating expiratory pressure relief process 86 in FIG. 3. In addition, FIG. 4C illustrates a VarPAP waveform 90 in which the inspiratory portion and the expiratory portions of the waveform are at the same pressure level, so that IPAP=EPAP. Thus, VarPAP waveform 90 effectively corresponds to a conventional CPAP waveform.

Referring back to FIG. 3, the patient flow $Q_{patient}$ is also provided to a peak flow detection process 92, which monitors the patient flow and identifies the peak flows $Q_{peak(current)}$ 94 occurring within that flow during the inspiratory portion of each respiratory cycle. See also FIGS. 5A and 5B. The level of the peak $Q_{peak(current)}$ during the inspiratory phase of each respiratory cycle is stored in a memory array in peak flow, time and PS storage process 96 in FIG. 3. In addition to storing the peak flow for each breath, a time stamp identifying when the peak flow occurred, and an indication of the level of pressure support being provided to the patient at that time are also stored in the memory array. The pressure support level ($PS_{level(current)}$) is determined as the difference between IPAP and EPAP. In other words, $PS_{level}$=IPAP−EPAP. As discussed below, this stored information is used in other process blocks to determine how well the pressure support system is functioning to treat CSR and to adjust the system parameters, if necessary.

Figure 1:
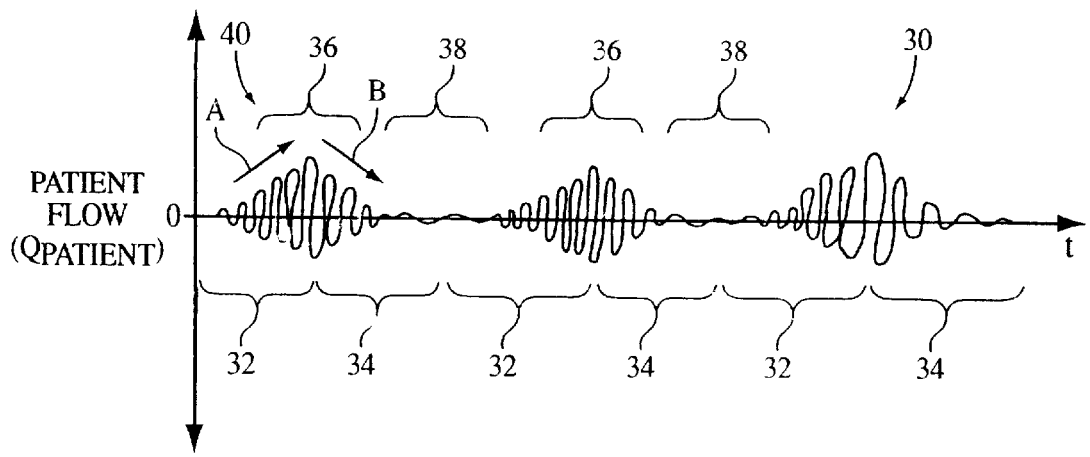
FIG. 1 illustrates a typical Cheyne-Stokes respiratory cycle that is treated by the pressure support system of the present invention.

As noted above, a characteristic of CSR is the presence of a hypopnea or apnea period 38 between the hyperpnea periods 36. See FIG. 1. These periods are often referred to as central apneas, because the cessation of respiration during these intervals is not believed to be due to an occluded airway. The VarPAP pressure support mode of the present invention addresses these periods of apnea in an automatic backup process 98. In automatic backup process 98, an I/E state signal, which indicates the respiratory state of the patient and, hence, identifies transitions between the states, is monitored. If a central apnea or cessation of respiratory effort is detected for a period of time, for example 5–12 seconds and referred to as the apnea detection time $T_{apnea}$, then a "machine breath" is automatically delivered to the patient by the pressure support system, thus ventilating the lungs. In the embodiment shown in FIGS. 5A and 5B, the apnea detection time $T_{apnea}$ begins at the end of each inspiration. If a period of time $T_{apnea}$ passes before the next spontaneous inspiration, a "machine breath" is automatically delivered to the patient. Such an event is generally indicated at 99 in FIG. 5B, where the $T_{apnea}$ period began at point I. Because a spontaneous inspiration had not occurred after the elapse of this period, a machine generated backup breath 101 was initiated at point J.

The apnea detection time $T_{apnea}$ is set manually or automatically based on that patient's prior breath rate, such as an average of the expiratory periods of the patient's last n breaths, where n is an integer. Once a machine breath is delivered to the patient, the pressure support system continues to deliver backup breaths at a back-up breath rate $T_{breath}$, with each machine generated "breath" having an inspiratory time $T_{insp}$. Typically, the backup breath rate $T_{breath}$ and the inspiratory time $T_{insp}$ are set by a clinician and are provided by the automatic backup process to the pressure support process, as indicated by signals 100, to control the operation of the pressure support system so that the system provides the machine generated breaths to the patient. Backup breaths cease when the patient begins breathing spontaneously, which is detected in pressure support process 72 and which appears as a change in the I/E state signal provided to automatic backup process 98.

Referring again to FIG. 3, according to the VarPAP algorithm of the present invention, the IPAP level is adjusted based on the results of a comparison between the last measured peak flow $Q_{peak(current)}$ and a target peak flow $Q_{peak(target)}$ in an IPAP adjustment process 102. The last measured peak flow $Q_{peak(current)}$ is received from peak flow detection process 92 and the target peak flow $Q_{peak(target)}$ is provided by a target peak flow and EPAP adjustment process 104 discussed in greater detail below. In a preferred embodiment of IPAP adjustment process 102, a change in the IPAP level ($\Delta$IPAP) is calculated during each respiratory cycle using the following equation:

$$\Delta IPAP = \text{Gain}(Q_{peak(target)} - Q_{peak(current)}), \quad (2)$$

where Gain is a fix gain determined empirically. In a preferred embodiment of the present invention, the Gain is selected as 9 cmH$_2$O. It is to be understood, that this gain can be varied, as needed, manually, or can be automatically adjusted over a prescribed range by the IPAP adjustment process.

Once the $\Delta$IPAP for a breath is calculated, the new IPAP level (IPAP$_{new}$) for the next following breathing is determined as IPAP$_{new}$=IPAP$_{previous}$+$\Delta$IPAP. Preferably, the rate of change for the IPAP level, i.e., the $\Delta$IPAP, is limited so that the patient is not presented with an abrupt change (increase or decrease) in the IPAP level. In a preferred embodiment of the present invention, $\Delta$IPAP is limited to ±3 cm H$_2$O. The new IPAP level is also checked against the established IPAP$_{max}$ and IPAP$_{min}$ levels. Note that IPAP$_{min}$ should not be less than the current EPAP level. The new IPAP level is then used by pressure support process 72 in the next inspiratory cycle. In this manner, the VarPAP pressure support algorithm continuously, at each respiratory cycle, searches for the appropriate IPAP level to be delivered to the patient based on the measured peak flow and a target peak flow.

It is to be understood that other techniques for adjusting the IPAP level in IPAP adjustment process 102 are contemplated by the present invention. For example, the current peak flow $Q_{peak(current)}$ can be compared to the target peak flow $Q_{peak(target)}$, and if $Q_{peak(current)}$ is less than $Q_{peak(target)}$, the IPAP level is increased. Likewise, if $Q_{peak(current)}$ is greater than $Q_{peak(target)}$, the IPAP level is decreased. Moreover, the amount by which the IPAP level is increased, i.e., the $\Delta$IPAP, can be variable depending on the amount by which $Q_{peak(current)}$ differs from $Q_{peak(target)}$. That is, the greater the difference, the greater the $\Delta$IPAP.

Ideally, the IPAP pressure control function of IPAP adjustment process 102 and the operation of automatic backup process 98 to treat the central apnea phase of the CSR cycle are sufficient to counteract the CSR. However, this may not be the case for all patients. In addition, the condition of each patient is dynamic. For these reasons, among others, the present invention includes the ability to adjust automatically the degree to which the pressure support system attempts to counteract the CSR cycle. This is accomplished by providing, in target peak flow and EPAP adjustment process 104, the ability to alter the target peak flow $Q_{peak(target)}$ used in IPAP adjustment process 102 automatically. The EPAP level can also be altered automatically, either alone or in combination with a target peak flow adjustment, by target peak flow and EPAP adjustment process 104 to treat the occurrence of CSR more effectively than in a system that uses a static EPAP level. The decision whether to adjust the target peak flow $Q_{peak(target)}$, the EPAP level, or both, and the amount to which they are adjusted is determined in target peak flow and EPAP adjustment process 104 based on the results of a performance parameter determination process 106.

In essence, in performance parameter determination process 106 the VarPAP pressure support mode assess the degree to which the patient is experiencing CSR, if at all, and based on this determination, the variable positive airway pressure support system adjusts the pressure support provided to the patient in target peak flow and EPAP adjustment process 104 by adjusting the target peak flow, the EPAP, level or both. As noted above, this process of measuring the effectiveness of the performance of the VarPAP mode of pressure support and process of adjusting the pressure support to increase its effectiveness, if necessary, is carried out every 2 to 5 minutes.

In a preferred embodiment of the present invention, performance parameter determination process 106 measures of the effectiveness of the pressure support therapy and determines the degree of pressure support intervention based on the following three parameters: 1) a CSR shape index, 2) a CSR severity index, and 3) a pressure support (PS) index. Each of these parameters is discussed in turn below. Based on the CSR shape index, the CSR severity index, PS index, the target peak flow and EPAP adjustment process will adjust either the target peak flow, the EPAP or both.

The CSR shape index is determined based on a coherence function, which is a mathematical tool for determining how well an unknown pattern is similar to a template pattern. In the present invention, the unknown pattern is a sequence of previously recorded peak flows, and the template pattern is a pattern selected to correspond to a CSR pattern. The CSR shape index, expressed as a percentage, is a measure of how well these two patterns coincide, and, hence, how well the peak flow data collected over the past several minutes corresponds to a CSR pattern; the closer the match, the more likely it is that the patient is experiencing CSR.

The coherence technique first requires acquiring the stored peak flows and associated data from peak flow, time and PS storage process 96 corresponding to the peak flows stored over the last 2–3 minutes. The peak flows are then processed to fit a typical CSR pattern of a least one cycle, approximately 60 sec. in duration. Depending on the CSR template, this requires that peak flows and times from the last 2–5 minutes to be stored in the array in peak flow, time and PS storage process 96. Using a normalized cross-correlation technique, the peak flows are compared to the CSR template, and a CSR shape index ranging from 0–100% is generated.

Figure 6A:
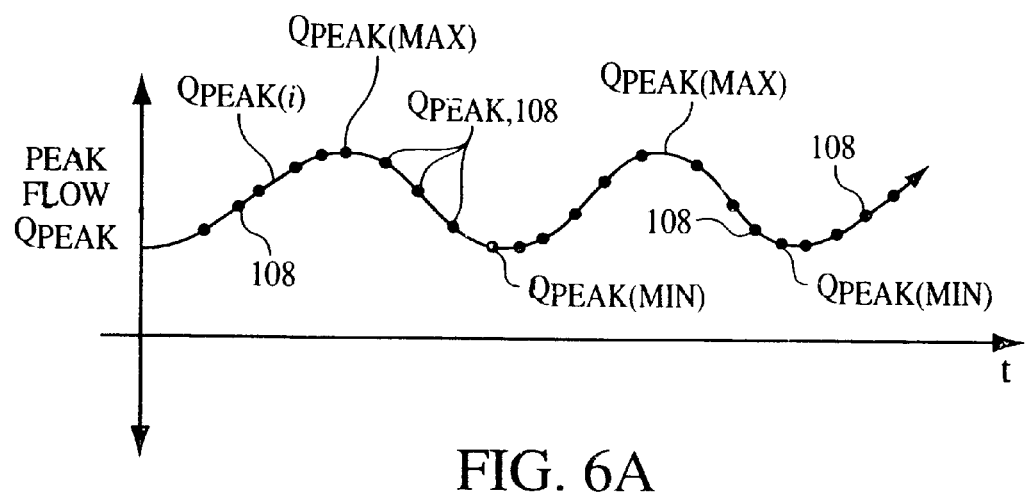
FIG. 6A is a chart showing an array of peak flow data collected by the variable positive airway pressure support system.
Figure 6B:
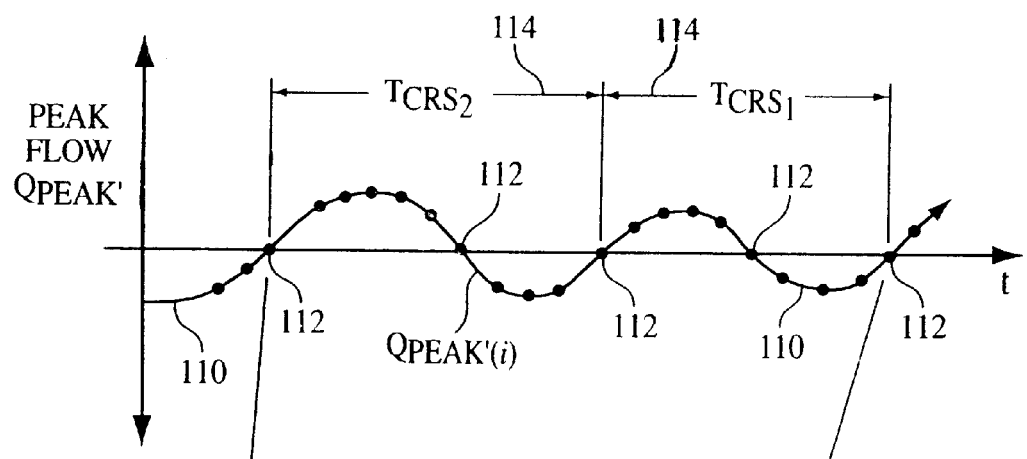
FIG. 6B is illustrates the array of peak flow data after a first DC bias removal process, and FIG. 6C illustrated the array of peak flow data normalized for comparison to an exemplary a CSR template waveform used by the system to gauge the effectiveness of the pressure support treatment.

FIG. 6A illustrates an array of peak flows 108 ($Q_{peak}(i)$) stored in peak flow, time and PS storage process 96 over the time interval of interest, which is typically the last 2–5 minutes. The peak flows 108 are processed to remove the "DC" bias in this array of peak flow flows, so that zero crossings 112 can be detected to yield a shifted array of peak flows 110 ($Q_{peak}'(i)$) shown in FIG. 6B. According to an exemplary embodiment of the present invention, the "DC" bias is removed by first searching the array of peak flow for minimum and maximum peak flow values $Q_{peak(min)}$ and $Q_{peak(max)}$, and then recalculating each peak flow $Q_{peak}'(i)$ according to the following equation:

$$Q_{peak}'(i) = Q_{peak}(i) - (Q_{peak(max)} - Q_{peak(min)})/2 + Q_{peak(min)}, \quad (3)$$

where i is the sample index. Of course, any conventional technique for effectively removing the DC bias, i.e., placing a zero line in the peak flow array $Q_{peak}(i)$ 108 at the appropriate location can be used, so that it is then possible to determine the zero crossings 112 of the shifted array of peak flows $Q'_{peak}(i)$ 110.

To find the zero crossings, the shifted array of peak flows $Q'_{peak}(i)$ 110 is searched, preferably starting at the most recent $Q_{peak}'(i)$ and working backwards in time, using a robust zero crossing (ZC) detection method. The first three zero crossings 112 having the same slopes are used to define the last two CSR cycles 114. Once a ZC is detected, it is also time-stamped. From the ZC time-stamps, the period $T_{CSR}$ of the CSR cycle is measured. The measured CSR periods are used to time-wrap each of the two CSR cycles on to the CSR template. Excessive time-warp due to the measured CSR period being out of range, e.g., 40–90 seconds, stops the process, and a CSR Index of 0% (zero) is returned.

The CSR template is a sequence of peak flows that describe the general shape of CSR. In a preferred embodiment of the present invention shown in FIG. 6C, simple triangle function is used as CSR template 116. It can be appreciated, however, that other templates can be used.

Figure 6C:
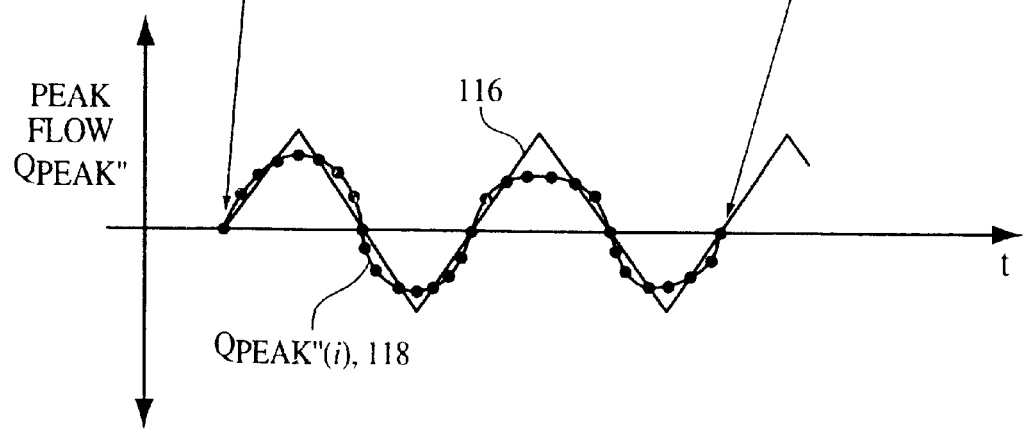

To time-warp the $Q_{peak}'(i)$ array, the time stamps and the $Q_{peak}'(i)$ values are used to map $Q_{peak}'(i)$ values on to the same sampling rate as the CSR template 116 using linear interpolation and, thus, a second array of peak flows $Q_{peak}''(i)$ 118 is produced as shown in FIG. 6C. To perform the correlation in the discrete-time domain, i.e., using digital samples, the samples in the peak flow array have to be time-aligned with those of CSR template 116. The coherence function, which provides an indication of the degree of difference between $Q_{peak}''(i)$ and the CSR template is computed. The result is called the CSR shape index, which is given in percent and ranges from 0 to 100%.

In summary, the peak values are stored in an array along with the timestamps of when the peaks occurred. Next, the first three zero-crossings are detected and the periods of the first two CSR cycles are computed. The peak flow array is recalculated and time-warped in order to fit the CSR template and the coherence function is computed yielding the CSR shape index.

The CSR severity index is calculated from the array of peak flows $Q_{peak}(i)$ 108 (FIG. 6A) as a ratio of the minimum peak flow $Q_{peak(min)}$, over the maximum peak flow, $Q_{peak(max)}$. The last minimum and maximum values or an average of several minimum and maximum values occurring in the array of peak flows during the sample interval can be used to determine the CSR severity index, which is also expressed as a percentage. In general, a CSR severity index greater than 50% is considered normal, less than 50% is abnormal and an index of 0% indicates the occurrence of a central apnea.

The pressure support (PS) index, unlike the CSR shape index and the CSR severity index, is not a measure of a parameter directly associated with the CSR cycle. Rather, the PS index is a measure of amount of assistance that is being provided by the pressure support system in attempting to combat the CSR cycle, i.e., how much the pressure support system is intervening on behalf of the patient to augment their ventilation. The amount of pressure support is determined as the difference between the IPAP and the EPAP levels of the pressure provided to the patient, i.e., PS=IPAP−EPAP. In a preferred embodiment, the PS index is determined as the percentage of breaths where the pressure support provided to the patient was above a threshold, typically 2 cmH$_2$O over the last 2–3 minutes or last 2 CSR cycles.

The CSR shape index, a CSR severity index, and PS index determined in performance parameter determination process 106, are provided to target peak flow and EPAP adjustment process 104, which determines whether to adjust the target peak flow $Q_{peak(target)}$, the EPAP level, or both based thereon. More specifically, in a target peak flow adjustment mode, the target peak flow and EPAP adjustment process uses the table shown in FIG. 7 to adjust the target peak flow based on the ranges for the CSR shape index, CSR severity index, and PS index. The EPAP level is not adjusted. The extreme right column 113 in FIG. 7 indicates the change $\Delta Q_{peak(target)}$ to be made at each adjustment depending on the ranges for the CSR shape index, CSR severity index, and PS index.

It should be noted that the present invention is not intended to be limited to the values shown for the change in the peak flow target $\Delta Q_{peak(target)}$, i.e., the values shown in column 113 in FIG. 7. On the contrary, those skilled in the art can appreciated that the change in the peak flow target can be modified according to clinical judgment.

If, however, the PS index is 70% or more for more than 6 minutes, the target peak flow is not adjusted. Instead, the target peak flow and EPAP adjustment process enters an EPAP adjustment mode. It is to be understood that the present invention is not intended to be specifically limited to the 70% and 6 minute selections for transitioning to the EPAP adjustment mode. On the contrary, those skilled in the art would understand that a range of index valves and time limits are possible.

In the EPAP adjustment mode, target peak flow and EPAP adjustment process 104 uses the table shown in FIG. 8 to adjust the EPAP level based on the ranges for the CSR shape index, CSR severity index, and PS index determined by performance parameter determination process 106. The extreme right column 115 in FIG. 8 indicates the change $\Delta$EPAP to be made at each adjustment. This EPAP change, or the new EPAP setting, is provided to pressure support process 72 as indicated by blocks 120a and 120b in FIG. 3. In this mode, the target peak flow $Q_{peak(target)}$ is decreased incrementally during each EPAP adjustment process by a predetermined amount, such as 1 liter per minute, until the PS index is less than 50%, for example.

It should be noted that the present invention is not intended to be limited to the values shown for the change in the EPAP level, i.e., the values shown in column 115 in FIG. 8. On the contrary, those skilled in the art can appreciated that the change in the EPAP can be modified according to clinical judgment.

As noted above, preferably maximum and minimum target peak flow $Q_{peak(target(max))}$, $Q_{peak(target(min))}$ and maximum and minimum EPAP levels are set so that the target peak flow and the EPAP levels are limited to a range of permissible, clinically safe, values.

The EPAP adjustment continues until 1) the CSR is resolved, as determined by performance parameter determination process 106, or 2) the EPAP level reaches its maximum for 6 minutes. Of course, other EPAP levels and time limits for determining when to end the EPAP adjustment mode can be selected depending on the desired degree at which the system attempts to correct the CSR pattern. When either of these conditions occur, the EPAP level is then decreased toward its minimum level, and the target peak flow and EPAP adjustment process 104 switches back to the target peak flow adjustment process, where EPAP remains constant and the target peak flow is adjusted according to the table shown in FIG. 7.

In an example of an application of the variable positive airway pressure support system, the preferred embodiment of the present invention is connected to a patient as shown in FIG. 2. A caregiver, such as an authorized clinician, doctor, or respiratory therapist, inputs a minimum and maximum IPAP and EPAP levels, as well as a minimum and maximum target peak flow $Q_{peak(target(max))}$, $Q_{peak(target(min))}$. Initially, the IPAP level is set to the minimum IPAP pressure, EPAP is set to the minimum EPAP pressure, and the target peak flow is set to the minimum target peak flow setting. If the minimum IPAP and EPAP levels are the same, the variable positive airway pressure support system operating in this VarPAP modes is essentially providing a CPAP pressure support treatment at that time, because IPAP=EPAP. The patient then falls asleep with the device running the VarPAP algorithm shown in FIG. 3. If the peak flow $Q_{peak}$ drops below the target peak flow value $Q_{peak(target)}$, IPAP is increased by an incremental amount for the next breath.

Figure 9:
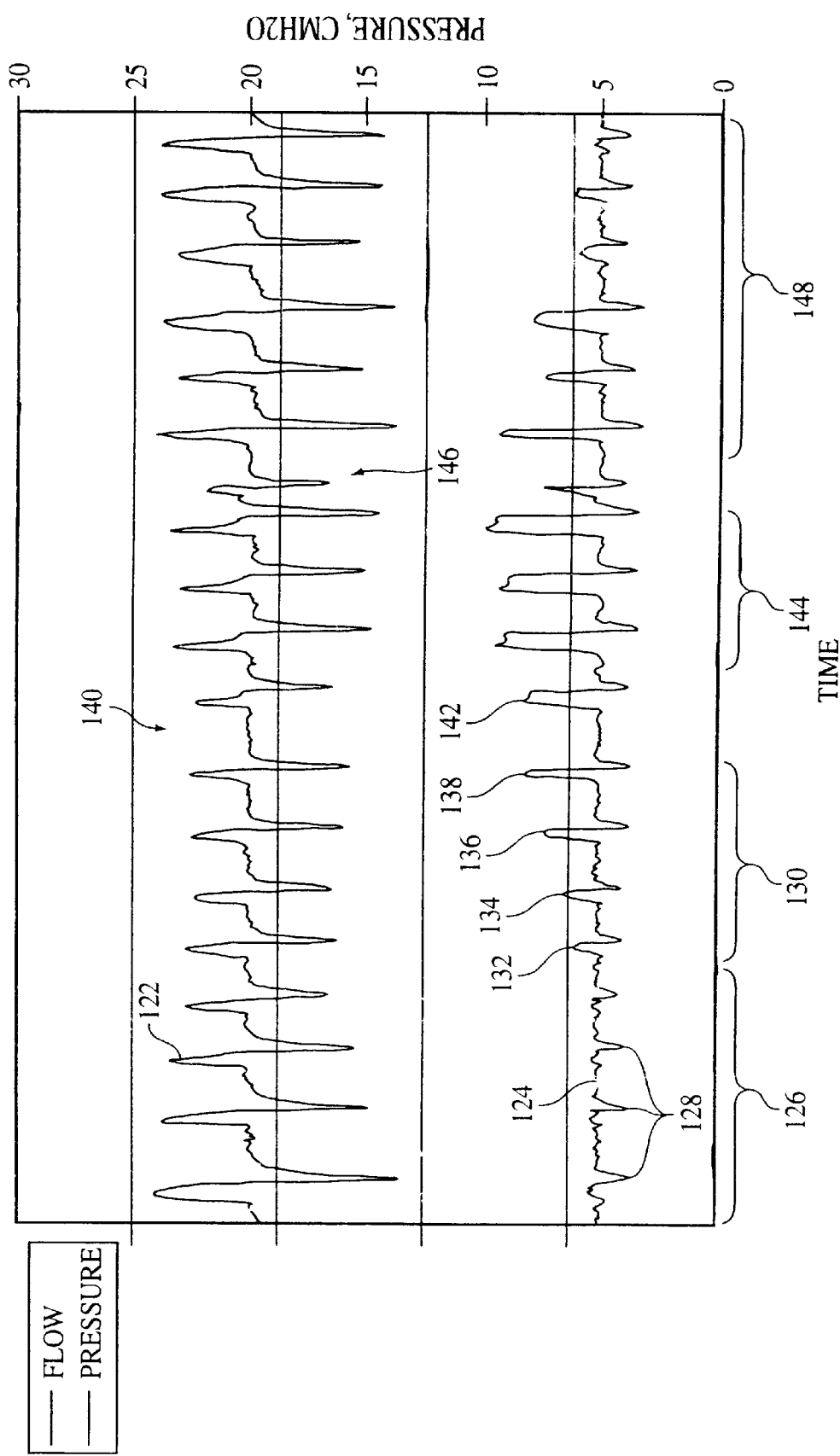
FIG. 9 is a chart illustrating the patient flow for a patient suffering from CSR and the pressure waveform output by the variable positive airway pressure support system of the present invention in response thereto.

FIG. 9 illustrates the patient flow $Q_{patient}$ 122 for a patient suffering from CSR and a pressure waveform 124 output by the variable positive airway pressure support system of the present invention in response thereto. In time interval 126, the patient is experiencing a decrescendo in his or her respiratory peak flows. During this interval, the IPAP level is at a minimum level and the EPAP level 128 is constant. However, at the start of time interval 130, the patient's peak flow falls below the target peak flow and IPAP level 132 in increased and continues to increase, as indicated by increasing IPAP peaks 134, 136, and 138 during interval 130. At a time, generally indicated at 140, the patient does not make an inspiratory effort, and a machine breath 142 is delivered by the pressure support system. In time interval 144, the patient receives additional machine generated breaths until a time 146, when the patient makes a spontaneous respiratory effort. During the subsequent time interval 148, the IPAP level is reduced back to its minimum.

Figure 10:
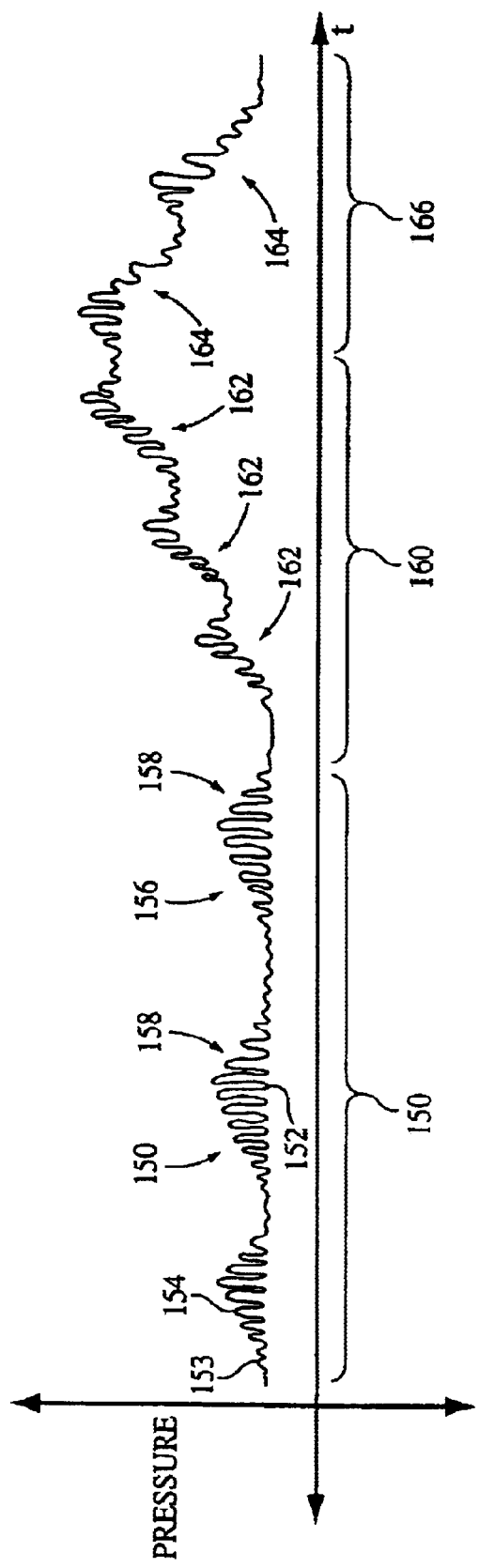
FIG. 10 is a pressure waveform illustrating exemplary changes to both IPAP and EPAP that can be accomplished by the variable positive airway pressure support system of the present invention.

Every 2 to 5 minutes, the patient flow is monitored using performance parameter determination process 106 to determine whether the patient's flow corresponds to a CSR pattern. If so, the target peak flow, EPAP, or both are altered as discussed above. FIG. 10 illustrates a pressure waveform 153 output by the pressure support system that includes changes to both IPAP and EPAP, according to the principles of the present invention. In this illustration, during time interval 150, the patient is receiving repeated patterns of pressure support where the EPAP level 152 is constant and the IPAP level 154 repeatedly increases, as generally indicated at 156, and decreases, as generally indicated at 158. During these intervals, the pressure support system determines, via performance parameter determination process 106 and target peak flow and EPAP adjustment process 104, that the patient is experiencing CSR and is continues to attempt to counteract the CSR by adjusting the target peak flow.

At the beginning of time interval 160, however, the system begins increasing the EPAP level, because altering the peak target flow was not sufficient to counteract the presence of CSR. In other words, the system has switched to the EPAP adjustment mode discussed above. During interval 160, the EPAP level increases, as generally indicated at 162, while the IPAP level also continues to be adjusted by IPAP adjustment process 102. Eventually, either the CSR pattern is resolved, or the $EPAP_{max}$ level is reached. In either event, the EPAP level is decreased, as generally indicated at 164, during interval 166. During this interval, the peak target pressure is also decreased. Thereafter, the pressure support system exits the EPAP adjustment mode and returns to the peak target pressure $Q_{peak(target)}$ adjustment mode.

As noted above, during the apnea period of the CSR cycle, a machine breath in delivered to the patient. When this occurs, special consideration must be given to the peak flows determined by peak flow detection process 92 in FIG. 3. If, for example, the peak flows resulting from the machine generated breaths are used for the patient's peak flow, this may not be an accurate representation of the patient's actual respiratory condition, because the machine generated peak flows are not indicative of the patient's respiratory effort. For this reason, when a machine breath is administered, the pressure support system sets the peak for $Q_{peak}$ to zero, i.e., $Q_{peak(current)}=0$, even though the measured peak flow $Q_{patient}$ corresponds to the peak flow produced from the machine generated breath. This prevents the peak flow array $Q_{peak}(i)$ (see FIG. 6A) from inaccurately resembling a normal patient flow pattern, especially during the central apnea portion of the CSR cycle. For later machine generated breaths, if any, the peak flow is not set to zero. Instead, the peak flow $Q_{peak(current)}$ is set to the measured peak flow minus a correction factor, which is a function of the peak flow in the second machine generated breath.

More specifically, the peak flow that corresponds to the second machine generated breath $Q_{peak}(t0)$ is determined according to the following equation:

$$Q_{peak}(t0)=Q_{peak}(t0)-G_{rs}*PS(t0), \qquad (4)$$

where PS(t0) is the pressure support at time t0 (PS(t0)=IPAP(t0)−EPAP(t0)), and $G_{rs}$ is determined as follows:

$$G_{rs} = \frac{Q_{peak}(t0)}{PS(t0)}. \qquad (5)$$

The peak flows that corresponds to the third, fourth, etc., machine generated breaths $Q_{peak}(t)$, which are, of course, after the second machine generated breath $Q_{peak}(t0)$, are determined according to the following equation:

$$Q_{peak}(t)=Q_{peak}(t)-G_{rs}*PS(t). \qquad (6)$$

It can be appreciated that the above-described techniques for implementing the VarPAP mode of pressure support controls the pressure support levels for IPAP and EPAP based on how closely a series of patient's peak flows correspond to a series of peak flows associated with CSR. This is determined, in particular, in performance parameter determination process 106 as discussed above. However, the present invention contemplates other techniques for determining whether the patient is actually experiencing CSR. An alternative CSR detection algorithm 168 to detect CSR, and, hence, control the target peak flow, EPAP, or both based thereon, is shown in FIG. 11.

Figure 11:
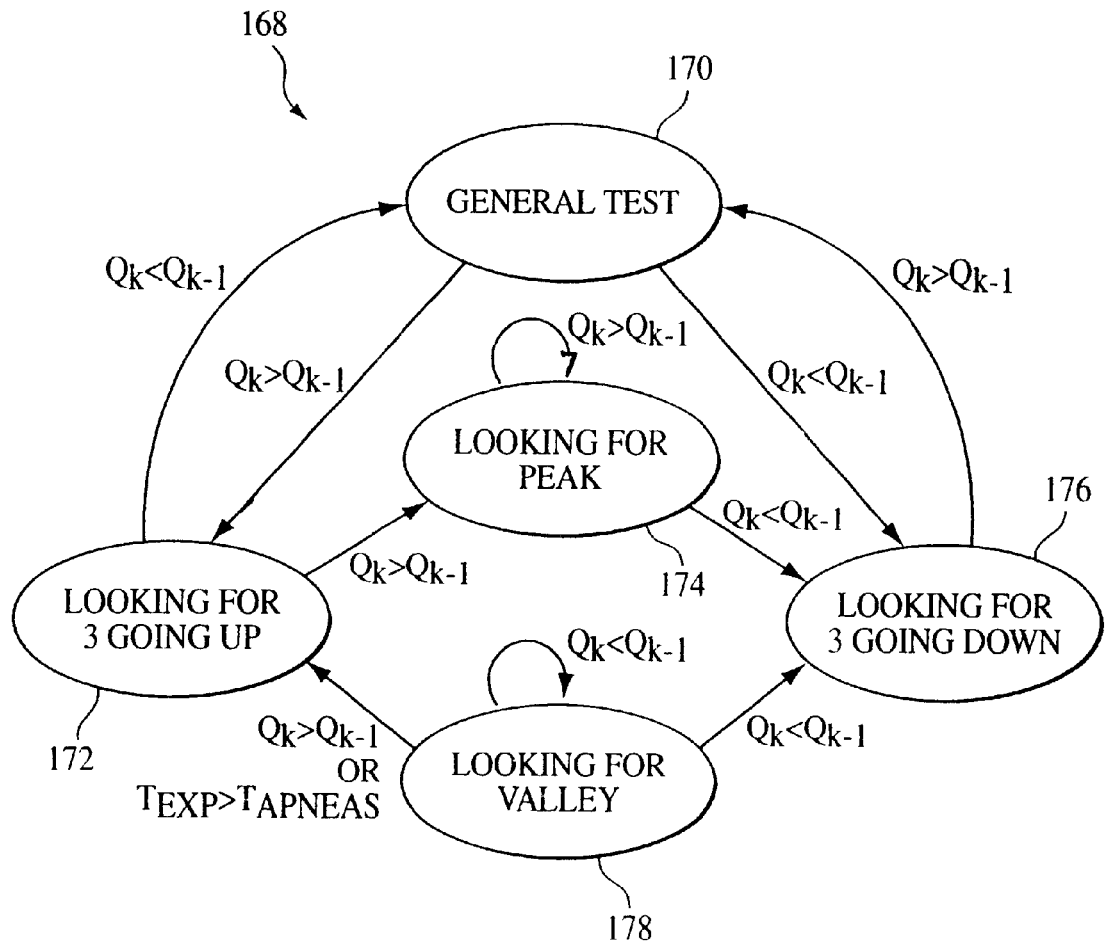
FIG. 11 is a diagram illustrating a CSR monitoring process according to a second embodiment of the present invention.

In this embodiment, the process shown in FIG. 11 is executed continuously to "look for" the CSR cycle. According to this technique, three consecutive increasing peak flows are considered an upward trend and likewise, three consecutive peak flows decreasing in value are considered a downward trend. This alternative algorithm detects the upward trend (crescendo), peak (hyperpnea), downward trend (decrescendo), and valley (hypopnea or apnea) of the CSR pattern. If the upward or downward trends are broken then the present apparatus resets. Otherwise, if the present apparatus completes two cycles, then the system determines that a CSR pattern is detected, and adjusts the target peak pressure or the EPAP level accordingly. For example, the target peak pressure is first adjusted to its maximum if CSR is detected. If this fails to counteract the CSR cycle, the EPAP level is then increased and the target peak pressure is lowered. All the while, IPAP adjustment process 102 continues to optimize the IPAP setting.

CSR detection in FIG. 11 begins in step 170, where the current peak flow $Q_{peak}(k)$, which is the peak flow for the current breath cycle, is compared to the previous peak flow $Q_{peak}(k-1)$, which is the peak flow for the immediately preceding breath cycle. If $Q_{peak}(k)$ is greater than $Q_{peak}(k-1)$, the process attempts to determine if there is a upward trend (crescendo) in step 172. If three consecutive reductions in peak flow are present, the process looks for a peak flow peak (hyperpnea) in step 174. Otherwise, the process returns to step 170. If a peak is detected in step 174, the process attempts to determine if there is a downward trend (decrescendo) in step 176. If three consecutive decreases in peak flow are present in step 176, the process looks for a peak flow valley (hypopnea or apnea) in step 178. If a peak in the peak flow is detected in step 178, the process begins looking again for three consecutive reductions in peak flow in step 172. If the cycle is completed two or more times, the patient is deemed to be experiencing CSR. A similar process is followed if $Q_{peak}(k)$ is less than $Q_{peak}(k-1)$ in step 170.

Some breathing patterns exhibit the CSR pattern but have minor fluctuations in peak flow. A true CSR pattern shows high peak flow followed by a very low peak flow or an apnea. Thus, in a preferred embodiment of the present invention, a further criteria, in which the maximum peak flow has to be above the threshold, must be met before the patient is considered to be experiencing that hyperpnea phase of a CSR pattern. Likewise, a still further criteria, in which the minimum peak flow has to be below the hypopnea level, must be met before the patient is considered to be experiencing that hyponea phase of a CSR pattern. These thresholds are determined by the clinician and typically based on observation of peak flows during sleep.

In a further embodiment of the present invention, the pressure support system is also adapted to implement other conventional modes of pressure support, such as CPAP, PPAP, BiPAP, for delivering the flow of breathing gas to treat sleep apnea, including obstructive sleep apnea and central apneas, CHF, COPD, or other cardio-pulmonary disorders, either alone or in conjunction with the novel VarPAP pressure support mode for treating CSR of the present invention.

The present invention contemplates that controller 26 implements many of the standard functions of a pressure support device, i.e., providing CPAP, bi-level pressure support BiPAP, PPAP pressure support, smart-CPAP as taught, for example, in U.S. Pat. Nos. 5,203,343; 5,458,137; and 6,087,747 all to Axe et al. the contents of which are incorporated herein by reference, or auto-CPAP as taught, for example, in U.S. Pat. No. 5,645,053 to Remmers et al. the contents of which are also incorporated herein by reference, in addition to implementing the VarPAP mode of pressure support. In one embodiment of the present invention, the pressure support system includes a mode select input device that allows a user or authorized caregiver to select the mode of ventilation (VarPAP, CPAP, bi-level, auto-CPAP) under which the pressure support device operates. However, the present invention also contemplates that pressure support system implements the VarPAP mode of pressure support alone. In addition, the present invention contemplates performing the CSR detection techniques in the background while implementing a conventional mode of pressure support and then switching the VarPAP mode of pressure support once CSR is detected.

If not otherwise stated herein, it may be assumed that all components and/or processes described heretofore may, if appropriate, be considered to be interchangeable with similar components and/or processes disclosed elsewhere in the specification, unless an indication is made to the contrary. It should be appreciated that the apparatus and methods of the present invention may be configured and conducted as appropriate for the application. The embodiments described above are to be considered in all respects only as illustrative and not restrictive. The scope of the invention is defined by the following claims rather than by the foregoing description. All changes which come within the meaning and range of equivalency of the claims are to be embraced within their scope.

What is claimed is:

1. A system for delivering a flow of breathing gas to an airway of a patient, the system comprising:

a gas flow generating system that generates a flow of breathing gas;

a patient circuit coupled to the gas flow generating system and adapted to communicate the flow of breathing gas to an airway of a patient;

a flow sensor associated with the gas flow generating system or the patient circuit and adapted to measure the flow of breathing gas within the patient circuit and to transmit a flow signal indicative thereof;

CSR monitoring means, receiving the flow signal from the flow sensor, for (1) determining peak flows $Q_{peak(current)}$ therefrom, and for determining whether such a patient's respiratory activity is indicative of Cheyne-Stokes respiration based on the peak flow $Q_{peak(current)}$; and controlling means for controlling the gas flow generating system so as to cause the breathing gas to be delivered at a sufficient pressure during at least a portion of a breathing cycle to threat Cheyne-Stokes respiration based on an output of the CSR monitoring means.

2. The system of claim 1, wherein the gas flow generating system includes:

a pressure generator adapted to generate the flow of breathing gas; and a pressure control valve associated with the pressure generator or the patient circuit to control a pressure of the flow of breathing gas delivered to a patient by the patient circuit.

3. The system of claim 1, wherein the CSR monitoring means sets a value for a target peak flow $Q_{peak(target)}$ based on whether such a patient's respiratory activity is indicative of Cheyne-Stokes respiration, and wherein the controlling means compares the inspiratory peak flow $Q_{peak(current)}$ to the target peak flow $Q_{peak(target)}$, and causes the gas flow generating system to adjust an inspiratory positive airway pressure (IPAP) based on the comparison between the inspiratory peak flow $Q_{peak(current)}$ and target peak flow $Q_{peak(target)}$.

4. The system of claim 3, wherein the controlling means detects I/E transitions between an inspiratory phase and an expiratory phase of a respiratory cycle, and causes the gas flow generating system to deliver a machine breath responsive to a failure to detect an a patient initiated between within a predetermined period of time.

5. The system of claim 3, wherein the CSR monitoring means monitors the efficacy of the delivering of pressurized breathing gas in the treatment of central apnea and Cheyne-Stokes respiration.

6. The system of claim 5, wherein the CSR monitoring means adjusts the value of the target peak flow $Q_{peak(target)}$, an expiratory positive airway pressure, or both, responsive to a determination that the delivering of pressurized breathing gas in the treatment is not effectively treating Cheyne-Stokes respiration.

7. The system of claim 1, wherein the CSR monitoring means determines magnitudes and times of inspiratory peaks flows and comparing these to a Cheyne-Stokes respiration pattern.

8. A method for delivering pressurized breathing gas to an airway of a patient, the method comprising the steps of:
  delivering a flow of gas to the airway of the patient from a source of breathing gas via a patient circuit;
  sensing a parameter indicative of a flow of gas within the patient circuit and outputting a flow signal;
  determining peak flows $Q_{peak(current)}$ in the flow of gas from the flow signal;
  monitoring whether such a patient's respiratory activity is indicative of Cheyne-Stokes respiration based on the peak flows $Q_{peak(current)}$; and
  controlling the delivery of gas so as to cause the breathing gas to be delivered at a sufficient pressure during at least a portion of a breathing cycle to treat Cheyne-Stokes respiration based on the detected peak flows and a result of the monitoring step.

9. The method of claim 8, wherein delivering a flow of gas includes generating a flow of breathing gas via a pressure generator and controlling a pressure of the flow of gas via (1) a pressure control valve associated with the pressure generator or the patient circuit, (2) controlling an operating speed of the pressure generator, or (3) a combination of both (1) and (2).

10. The method of claim 8, wherein monitoring whether such a patient's respiratory activity is indicative of Cheyne-Stokes respiration includes determining a target peak flow $Q_{peak(target)}$, and wherein controlling the delivery of gas includes comparing the inspiratory peak flow $Q_{peak(current)}$ to the target peak flow $Q_{peak(target)}$, and adjusting an inspiratory positive airway pressure (IPAP) based on the comparison between the inspiratory peak flow $Q_{peak(current)}$ and target peak flow $Q_{peak(target)}$.

11. The method of claim 10, further comprising:
  detecting I/E transitions between an inspiratory phase and an expiratory phase of a respiratory cycle; and
  delivering a machine generated breath to a patient responsive to a failure to detect an a patient initiated between within a predetermined period of time.

12. The method of claim 10, wherein monitoring whether such a patient's respiratory activity is indicative of Cheyne-Stokes respiration includes monitoring the efficacy of the delivering of pressurized breathing gas in the treatment of central apnea and Cheyne-Stokes respiration.

13. The method of claim 12, wherein monitoring whether such a patient's respirtory activity is indicative of Cheyne-Stokes respiration includes adjusting the target peak flow $Q_{peak(target)}$, an expiratory positive airway pressure, or both, responsive to a determination the delivering of pressurized breathing gas in the treatment is not effectively treating Cheyne-Stokes respiration.

14. The method of claim 8, wherein monitoring whether such a patient's respiratory activity is indicative of Cheyne-Stokes respiration includes determining magnitudes and times of inspiratory peaks flows and comparing these to a Cheyne-Stokes respiration pattern.

* * * * *

UNITED STATES PATENT AND TRADEMARK OFFICE
CERTIFICATE OF CORRECTION

PATENT NO.   : 6,752,151 B2
DATED        : August 4, 2004
INVENTOR(S)  : Hill

It is certified that error appears in the above-identified patent and that said Letters Patent is hereby corrected as shown below:

Column 1,
Line 17, after "suited" insert -- to --.

Column 4,
Line 5, delete "an" and change "between" to -- inspiration --.

Column 11,
Line 5, delete "an" and change "between" to -- inspiration --.

Column 16,
Line 21, - change "threat" to -- treat --.

Signed and Sealed this

Seventh Day of September, 2004

JON W. DUDAS
*Director of the United States Patent and Trademark Office*